(12) United States Patent
Eriksson et al.

(10) Patent No.: US 7,141,422 B2
(45) Date of Patent: Nov. 28, 2006

(54) TRANSGENIC TREES EXHIBITING INCREASED GROWTH, BIOMASS PRODUCTION AND XYLEM FIBRE LENGTH, AND METHODS FOR THEIR PRODUCTION

(75) Inventors: Maria Eriksson, Umeå (SE); Thomas Moritz, Umeå (SE); Maria Israelsson, Umeå (SE); Olof Olsson, Göteborg (SE)

(73) Assignee: SweTree Technologies AB, Umea (SE)

( * ) Notice: Subject to any disclaimer, the term of this patent is extended or adjusted under 35 U.S.C. 154(b) by 564 days.

(21) Appl. No.: 10/221,296

(22) PCT Filed: Mar. 2, 2001

(86) PCT No.: PCT/SE01/00451

§ 371 (c)(1),
(2), (4) Date: Jan. 27, 2003

(87) PCT Pub. No.: WO01/66777

PCT Pub. Date: Sep. 13, 2001

(65) Prior Publication Data

US 2003/0172402 A1 Sep. 11, 2003

(30) Foreign Application Priority Data

Mar. 7, 2000 (SE) .................................... 0000751

(51) Int. Cl.
 C12N 15/82 (2006.01)
 C12N 5/04 (2006.01)
(52) U.S. Cl. ........................................ 435/419; 800/260
(58) Field of Classification Search ................ 800/298, 800/278, 287; 435/419, 468
 See application file for complete search history.

(56) References Cited

FOREIGN PATENT DOCUMENTS

WO  WO 94/28141  12/1994

OTHER PUBLICATIONS

Walden et al (1995, TIBTECH 13:324-331).*
Ahuja et al (1996, M.R. Ahuja et al (eds.) Somatic Cell Genetics and Molecular Genetics of Trees, Kluwer Academic Publishers. Netherlands. pp. 89-96).*
Coles, Jeremy P. et al. (1999) "Modification of gibberellin production and plant development in *Arabidopsis* by sense and antisense expression of gibberellin 20-oxidase genes" *The Plant Journal* 17(5): 547-556.
Eriksson, Maria E. (Jul. 2000) "Increased gibberellin biosynthesis in transgenic trees promotes growth, biomass production and xylem fiber length" *Nature Biotechnology* 18: 784-788.
Huang, Shihshieh et al. (1998) "Overexpression of 20-Oxidase Confers a Gibberellin-Overproduction Phenotype in Arabidopsis" *Plant Physiol.* 118: 773-781.
Fladung, M. (Sep. 1999) "Transgenic Trees for a Better World?," Proc. of the Intern. Congress "Application of Biotechnology to Forest Genetics" (Biofor-99), Vitoria-Gasteiz, Spain, Sep. 22-25, 1999, pp. 339-345.
Ellis, Dave et al. (2001) "Transgenic Trees: Where are We Now?," Proceedings of the First International Symposium on Ecological and Societal Aspects of Transgenic Plantations, Oregon State University, 2001, pp. 113-123.

* cited by examiner

*Primary Examiner*—Stuart F. Baum
(74) *Attorney, Agent, or Firm*—Morrison & Foerster LLP (57) ABSTRACT

Important aims in nearly all tree-breeding programs around the world are to produce plants with increased growth rates and stem volumes, and shorter rotation times. Such trees would yield more biomass per area unit. Here the present inventors have shown that when over-expressing a key regulatory gene in the biosynthesis of the plant hormone gibberellin (GA) in hybrid aspen (*Populus tremula*×*P. tremuloides*), improvements in valuable traits such as growth rate and biomass are obtained. In addition, these trees also have longer xylem fibers than unmodified wild type plants. Long fibres are very desirable in the production of strong paper, but it has not (as yet) proved possible to influence this trait by traditional breeding techniques. A further advantage of the present invention is that it may reduce or eliminate the use of growth influencing chemicals in forestry.

3 Claims, 6 Drawing Sheets

SEQUENCE LISTING

```
<160> NUMBER OF SEQ ID NOS: 2

<210> SEQ ID NO 1
<211> LENGTH: 1259
<212> TYPE: DNA
<213> ORGANISM: Artificial Sequence
<220> FEATURE:
<223> OTHER INFORMATION: Arabidopsis GA 20-oxidase cDNA construct
```

<400> SEQUENCE: 1

```
aatctctcaa aatggccgta agtttcgtaa caacatctcc tgaggaagaa gacaaaccga      60
agctaggcct tggaaatatt caaactccgt taatcttcaa cccttcaatg cttaaccttc     120
aagccaatat cccaaaccaa ttcatctggc ctgacgacga aaaaccttcc atcaacgttc     180
tcgagcttga tgttcctctc atcgaccttc aaaaccttct ctctgatcca tcctccactt     240
tagatgcttc gagactgatc tctgaggcct gtaagaagca cggtttcttc ctcgtggtca     300
atcacggcat cagcgaggag cttatatcag acgctcatga atacacgagc cgcttctttg     360
atatgcctct ctccgaaaaa cagagggttc ttagaaaatc cggtgagagt gttggctacg     420
caagcagttt caccggacgc ttctccacca agcttccatg gaaggagacc ctttctttcc     480
ggttttgcga cgacatgagc cgctcaaaat ccgttcaaga ttacttctgc gatgcgttgg     540
gacatgggtt tcagccattt gggaaggtgt atcaagagta ttgtgaagca atgagttctc     600
tatcattgaa gatcatggag cttctcgggc taagtttagg cgtaaaacgg gactacttta     660
gagagttttt cgaagaaaac gattcaataa tgagactgaa ttactaccct ccatgtataa     720
aaccagatct cacactagga acaggacctc attgtgatcc aacatctctt accatccttc     780
accaagacca tgttaatggc cttcaagtct ttgtggaaaa tcaatggcgc tccattcgtc     840
ccaaccccaa ggcctttgtg gtcaatatcg gcgatacttt catggctcta tcgaacgata     900
gatacaagag ctgcttgcac cgggcggtgg tgaacagcaa gagcgagagg aagtcacttg     960
cattcttctt gtgtccgaaa aaagacagag tagtgacgcc accgagagag cttttggaca    1020
gcatcacatc aagaagatac cctgacttca catggtctat gttccttgag ttcactcaga    1080
aacattatag agcagacatg aacactctcc aagccttttc agattggctc accaaaccca    1140
tctaagaaat aaaatattca tgtcttgtct tgttagttac tagtatcttc tttatatttc    1200
atgtatgtat atggtaatag gcaataacac cttttagcat ctcaaaaaaa aaaaaaaaa    1259
```

<210> SEQ ID NO 2
<211> LENGTH: 377
<212> TYPE: PRT
<213> ORGANISM: Artificial Sequence
<220> FEATURE:
<223> OTHER INFORMATION: Arabidopsis GA 20-oxidase cDNA construct

<400> SEQUENCE: 2

```
Met Ala Val Ser Phe Val Thr Thr Ser Pro Glu Glu Asp Lys Pro
  1               5                  10                  15

Lys Leu Gly Leu Gly Asn Ile Gln Thr Pro Leu Ile Phe Asn Pro Ser
                 20                  25                  30

Met Leu Asn Leu Gln Ala Asn Ile Pro Asn Gln Phe Ile Trp Pro Asp
             35                  40                  45

Asp Glu Lys Pro Ser Ile Asn Val Leu Glu Leu Asp Val Pro Leu Ile
 50                  55                  60

Asp Leu Gln Asn Leu Leu Ser Asp Pro Ser Ser Thr Leu Asp Ala Ser
 65                  70                  75                  80

Arg Leu Ile Ser Glu Ala Cys Lys Lys His Gly Phe Phe Leu Val Val
                 85                  90                  95

Asn His Gly Ile Ser Glu Glu Leu Ile Ser Asp Ala His Glu Tyr Thr
            100                 105                 110

Ser Arg Phe Phe Asp Met Pro Leu Ser Glu Lys Gln Arg Val Leu Arg
            115                 120                 125
```

-continued

```
Lys Ser Gly Glu Ser Val Gly Tyr Ala Ser Ser Phe Thr Gly Arg Phe
130                 135                 140

Ser Thr Lys Leu Pro Trp Lys Glu Thr Leu Ser Phe Arg Phe Cys Asp
145                 150                 155                 160

Asp Met Ser Arg Ser Lys Ser Val Gln Asp Tyr Phe Cys Asp Ala Leu
                165                 170                 175

Gly His Gly Phe Gln Pro Phe Gly Lys Val Tyr Gln Glu Tyr Cys Glu
            180                 185                 190

Ala Met Ser Ser Leu Ser Leu Lys Ile Met Glu Leu Leu Gly Leu Ser
        195                 200                 205

Leu Gly Val Lys Arg Asp Tyr Phe Arg Glu Phe Phe Glu Glu Asn Asp
    210                 215                 220

Ser Ile Met Arg Leu Asn Tyr Tyr Pro Pro Cys Ile Lys Pro Asp Leu
225                 230                 235                 240

Thr Leu Gly Thr Gly Pro His Cys Asp Pro Thr Ser Leu Thr Ile Leu
                245                 250                 255

His Gln Asp His Val Asn Gly Leu Gln Val Phe Val Glu Asn Gln Trp
            260                 265                 270

Arg Ser Ile Arg Pro Asn Pro Lys Ala Phe Val Val Asn Ile Gly Asp
        275                 280                 285

Thr Phe Met Ala Leu Ser Asn Asp Arg Tyr Lys Ser Cys Leu His Arg
    290                 295                 300

Ala Val Val Asn Ser Lys Ser Glu Arg Lys Ser Leu Ala Phe Phe Leu
305                 310                 315                 320

Cys Pro Lys Lys Asp Arg Val Val Thr Pro Pro Arg Glu Leu Leu Asp
                325                 330                 335

Ser Ile Thr Ser Arg Arg Tyr Pro Asp Phe Thr Trp Ser Met Phe Leu
            340                 345                 350

Glu Phe Thr Gln Lys His Tyr Arg Ala Asp Met Asn Thr Leu Gln Ala
        355                 360                 365

Phe Ser Asp Trp Leu Thr Lys Pro Ile
370                 375
```

TRANSGENIC TREES EXHIBITING INCREASED GROWTH, BIOMASS PRODUCTION AND XYLEM FIBRE LENGTH, AND METHODS FOR THEIR PRODUCTION

The present invention concerns transgenic trees exhibiting improved properties, and in particular properties of economic importance, such as increased growth rate, biomass production and xylem fibre length; transgenic plants, seeds, plant cells and other types of propagating material, as well as methods for their production.

BACKGROUND

A major disadvantage with traditional tree breeding, especially for forest tree species, is the slow progress due to their long generation periods. However, by taking advantage of recent developments in gene technology the time required to produce a new variety could be reduced significantly. In addition, a biotechnological approach would allow closer targeting of traits considered desirable by the forest and pulp industries, in specific tree species.

To date, most applications of genetic engineering of trees have focused on modifying lignin biosynthesis, resulting in trees with less lignin or a modified lignin composition, earlier flowering, pest or herbicide resistance. In order to change growth and development processes in trees, the manipulation of plant hormone levels, or the hormone sensitivity, would also be of interest. However, as yet there has only been few examples of the modification of plant hormone levels in trees. These have mainly been accomplished by directly altering endogenous IAA biosynthesis or cytokinin biosynthesis or indirectly by modifying various hormone pools using the *Agrobacterium rolC* gene. Although such modifications in all cases lead to trees with altered growth characteristics and wood properties, so far no improvements with a clear practical application have been obtained.

Gibberellins (GAs) are a group of more than 100 tetracyclic diterpenes, some of which are essential endogenous regulators that influence growth and development processes throughout the plant life cycle, e.g. shoot elongation, the expansion and shape of leaves, flowering and seed germination. The best examples illustrating the importance of GAs in control of shoot elongation are GA-deficient mutants of *Arabidopsis*, maize and pea. These have reduced levels of active GA(s) compared to wild type plants, resulting in a dwarfed phenotype due to a reduction in internode length. The phenotype of such GA-deficient mutants can be completely restored by the application of an active GA. At the cellular level, GAs have been found to promote both cell division and cell elongation.

Figure 1:
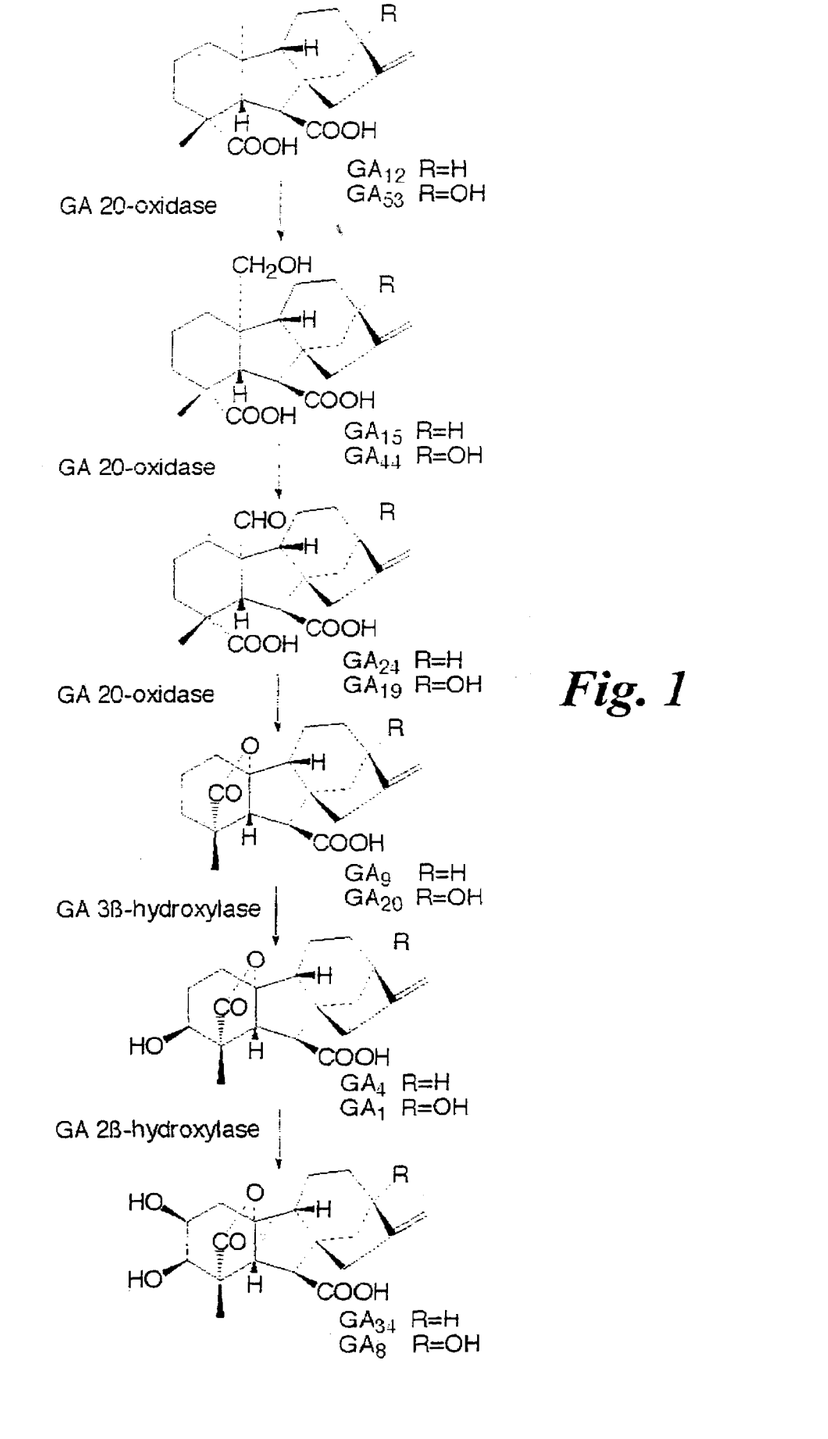
FIG. 1 shows the biosynthetic pathways converting $GA_{12}$ and $GA_{53}$ to the biologically active products $GA_4$ and $GA_{12}$, and their deactivated catabolites, $GA_{34}$ and $GA_8$, GA 20-oxidase catalyses the oxidation at the C-20 carbon.

Biosynthesis of GAs in planta occurs through the isoprenoid pathway from mevalonic acid. Gibberellin levels are mainly regulated by transcriptional control of gibberellin biosynthesis genes. In particular, the multifunctional enzyme gibberellin 20-oxidase (GA 20-ox) is a key-enzyme in controlling GA biosynthesis (FIG. 1). It catalyses the stepwise conversion of the C-20 gibberellins, $GA_{12}/GA_{53}$, by three successive oxidations to $GA_9/GA_{20}$, which are the immediate precursors of the active gibberellins, $GA_4$ and $GA_1$, respectively. The expression of the GA 20-oxidase gene is down regulated by the action of $GA_{14}$, suggesting that direct end-product repression is involved in regulation of the gene. In addition, some authors have suggested that GA 20-oxidase is photoperiodically regulated at the transcription level.

Application of chemicals that alter GA levels in the plant is a common practise in traditional agriculture and horticulture. Inhibitors of GA biosynthesis are especially commonly used as growth retardants in cereals and ornamental plants. In order to reduce the use of these chemicals, a biological approach like genetic modification of endogenous GA biosynthesis would have clear advantages. Using *Arabidopsis* as a model organism it has been shown that it is possible to change GA levels by modifying GA 20-oxidase enzyme levels and that this results in plants with altered growth and development patterns. Transgenic *Arabidopsis* expressing the GA 20-oxidase in a sense orientation shows earlier flowering and taller stems than wild type plants, whereas antisense plants have the reverse properties [Coles, J. P. et al. Modification of gibberellin production and plant development in *Arabidopsis* by sense and antisense expression of gibberellin 20-oxidase genes, *Plant J.* 17, 547–556 (1999)].

Modification of GA biosynthesis in a higher species, such as trees would be of additional interest since this would open up ways to modify wood. Previous hormone application studies have shown that GAs are required for the differentiation of xylem fibres, and that they have pronounced effects on the length of secondary xylem fibres and on both longitudinal and radial growth in hard wood species and conifers.

Obviously there remains a need for improved methods for modification of the growth properties of trees, in particular properties of technical and economical interest, such as growth rate, biomass increase and fibre length. Likewise, there remains a need of transgenic trees, exhibiting improved properties, such as increased growth rate, stem volume and xylem fibre length. Consequently, the objective of the present invention is to provide such improved methods and transgenic trees. Another objective is to reduce or eliminate the use of growth influencing chemicals in forestry.

PRIOR ART

It has been shown (Huang, S. et al., Overexpression of 20-Oxidase confers a gibberellin-overproduction phenotype in *Arabidopsis*, Plant Physiol., 1998, vol. 118, p 773–781) that the level of active GAs were raised following overexpression of GA 20-oxidase in *Arabidopsis thaliana*. This finding is however not directly tranferable on the present invention.

Most dicotyledons and all gymnosperm undergo some degree of secondary thickening. The amount of thickening depends on whether the mature plant is a herbaceous or a woody (arborescent) plant. For example an *Arabidopsis* plant will only produce secondary thickening under special conditions whereas a woody species, for example *Populus*, will undergo a high degree of secondary growth. The low degree of secondary thickening in herbaceous species will also make it very difficult to predict how specific genetic changes in herbaceous species corresponds in woody species in regards to changes in wood formation.

As an example, by over expressing the GA 20-oxidase in *Arabidopsis thaliana* the level of active GAs in the plant can be raised, as shown by Huang et al. (Supra). The transgenic plant phenotype included a dramatic cell elongation in all tissues. The petioles, inflorescence stems and leaves all showed cell elongation. It is clear from these results that the enhanced gibberellin levels have an effect on cell elongation from germination. However, from these results it is impossible to predict what the effect of GA 20-oxidase over expression in a woody plant would be. Cell division in the cambial mersistem in a woody plant is under the control of several different hormones and physical constraints not found in an annual plant such as *Arabidopsis thaliana*.

It was therefore surprising that there would be increased cell elongation of cells (fibres) originating from the cambium, and that it would be an increase in biomass caused by increased cambial cell division. It would not be obvious to one skilled in the art to over express GA 20-oxidase to increase wood biomass and fibre elongation.

Increase in the diameter of tree stems occurs primarily from meristematic activity in the vascular cambium, a cylindrical lateral meristem located between the xylem and phloem of the stem, branches, and woody roots. Two types of cell division occur in the cambium: additive and multiplicative. Additive division involves periclinal division of fusiform cambial initials to produce xylem and phloem mother cells that in turn divide to produce xylem and phloem cells. Multiplicative division involves anticlinal division of fusiform initials that provide for circumferential expansion of the cambium. After xylem and phloem cells are cut off by the cambial mother cells, they differentiate in an ordered sequence of events that includes cell enlargement, secondary wall formation, lignification and loss of protoplasts. These events do not occur stepwise, but rather as overlapping phases.

SUMMARY OF THE INVENTION

It is an object of the present invention to provide transgenic plants, seeds and plant cells, exhibiting improved growth parameters and in particular improved parameters of economical interest, such as increased growth rate, biomass increase and xylem fibre length. It is another object of the invention to provide a method for the production and proliferation of said transgenic plants. The above objects and others not explicitly mentioned, are fulfilled through a transgenic woody plant having a DNA sequence coding for the expression of a polypeptide exhibiting GA 20-oxidase activity functionally inserted in the plant genome. Further embodiments are as defined in the attached dependent and independent claims, incorporated herein by reference.

Other features and advantages of the invention will be apparent form the following, non-limiting description and examples, and from the claims.

BRIEF DESCRIPTION OF THE DRAWINGS

The invention will be described in closer detail below, in the description and accompanying examples and drawings, in which.

DESCRIPTION OF THE INVENTION

The present inventors have surprisingly shown that ectopic over-expression of a GA 20-oxidase gene in trees, here exemplified by a temperate-zone deciduous tree, results in significant changes in growth rate, stem volume and xylem fibre length. A cDNA sequence (SEQ. ID. NO. 1) homologous to the *Arabidopsis thaliana* GA 20 oxidase sequence X83379 (EMBL accession number) encoding a polypetide exhibiting GA 20 oxidase activity was used. Thus, the results obtained by the present inventors show that genetic modification of GA levels in trees can be used to modify traits that are extremely important for the forest, pulp and paper industries.

The results show that an endogenous elevation of the biologically active gibberellins $GA_1$ and $GA_4$ in trees will accelerate growth. This was demonstrated by expressing the AtGA20ox1 gene from *Arabidopsis* in hybrid aspen, *Populus tremula×tremuloides*, resulting in trees with faster height and diameter growth, larger leaves, longer xylem fibres and increased biomass. This phenotype is partly reminiscent of traits previously observed in transgenic *Arabidopsis* plants over-expressing the same GA 20-oxidase (Coles, J. P. et al., Modification of gibberellin production and plant development in *Arabidopsis* by sense and antisense expression of gibberellin 20-oxidase genes, *Plant J.* 17, 547–556 (1999). Such plants had longer hypocotyls, larger rosette leaves, longer petioles, and accelerated flowering compared to wild type plants.

However, studies regarding biomass increase and anatomical changes in transgenic *Arabidopsis* have not been reported. It is highly doubtful if an increased biomass would be achieved in transgenic *Arabidopsis*.

There have been suggestions that the GA 20-oxidase is a key enzyme in the regulation of GA controlled growth [Hedden, P. & Kamniya, Y. Gibberellin biosynthesis: Enzymes, genes and their regulation, *Annu. Rev. Plant Physiol. Plant Mol. Biol.* 48, 431–460 (1997)]. The fact that transcription of the GA 20-oxidase gene is feedback regulated by the action of GAs, suggests that constitutive over-expression of the GA 20-oxidase gene will disturb the endogenous regulation of GA homeostasis. Here, over-expression of GA 20-oxidase in hybrid aspen resulted in an increase in $C_{19}$-GAs involved in both the early 13-hydroxylation pathway and the non-13-hydroxylation pathway (FIG. 1). Thus, there was no consistent difference in levels between $GA_1$ and $GA_4$, both of which are biologically active in *Populus*. The present results therefore are in agreement with previous GA measurements on transgenic GA 20-oxidase overproducing *Arabidopsis* plants. Furthermore, in both hybrid aspen and *Arabidopsis* there was a dramatic increase in the levels of the deactivated end-product, $GA_8$ (Table 1).

This has been suggested to be due to a slower turnover of $GA_8$ than $GA_1$. The relatively low levels of the other end-product, $GA_{34}$, formed by the non-13-hydroxylation pathway can be explained by a more rapid turnover of this compound than $GA_8$. In contrast to the $C_{19}$-GAs, a decrease in levels of $C_{20}$-GAs was observed in the transgenic plants. This is consistent with the fact that $C_{20}$-GAs are, by definition, substrates for the GA 20-oxidase (Table 1).

It is surprising that the elevated GA 20-oxidase expression has such marked effects in *Populus tremula×tremuloides*. This suggests that constitutive over-expression of the GA 20-oxidase gene disturb the endogenous regulation of GA homeostasis.

In the present study the inventors found differences in GA levels between leaf and stem tissues: increases in levels of the active $GA_1$ and $GA_4$ being highest in stem tissue. This could have been due to the AtGA20ox1 gene being expressed most strongly in the stem. In hybrid aspen, however, the CaMV 35S promoter is generally slightly more active in leaves than in the stem, although exceptions are known to occur. Therefore, the higher $GA_1$ and $GA_4$ levels in the stem are more likely due to differences in transport of GAs or in the biosynthesis of GA precursors. However, it can not be ruled out that there may be a difference in GA 3β-hydroxylase or GA 2β-hydroxylase activity in the leaves. In *Arabidopsis* it has been shown that 2β-hydroxylation is activated at the transcriptional level by active GAs.

Figure 3:
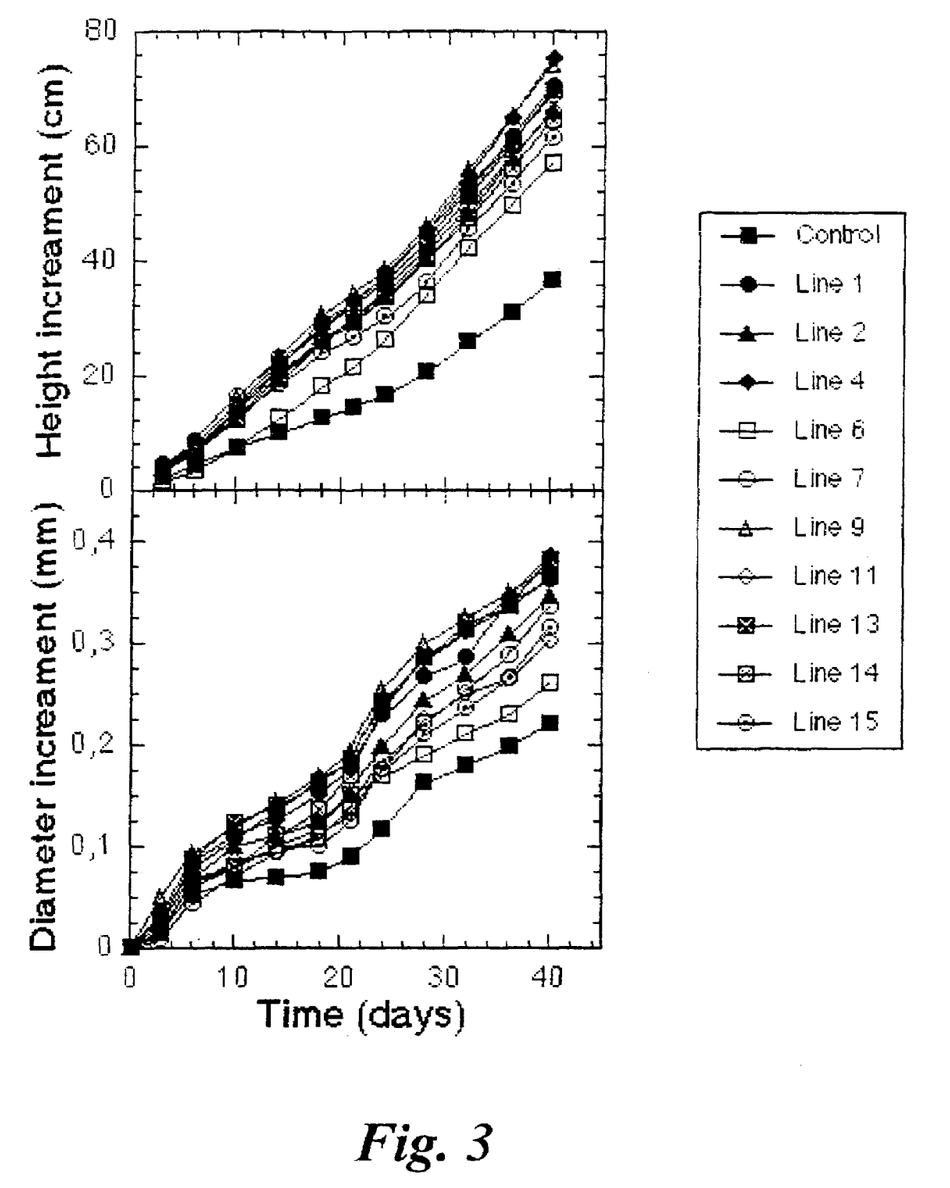
FIG. 3 shows the enhanced growth of transgenic hybrid aspen: the cumulative shoot elongation (upper diagram) and diameter growth (lower diagram) of various transgenic GA 20-oxidase over-expressing lines, after generation from tissue culture, potting and cultivation in a growth chamber for seven weeks (at time zero).
Figure 5:
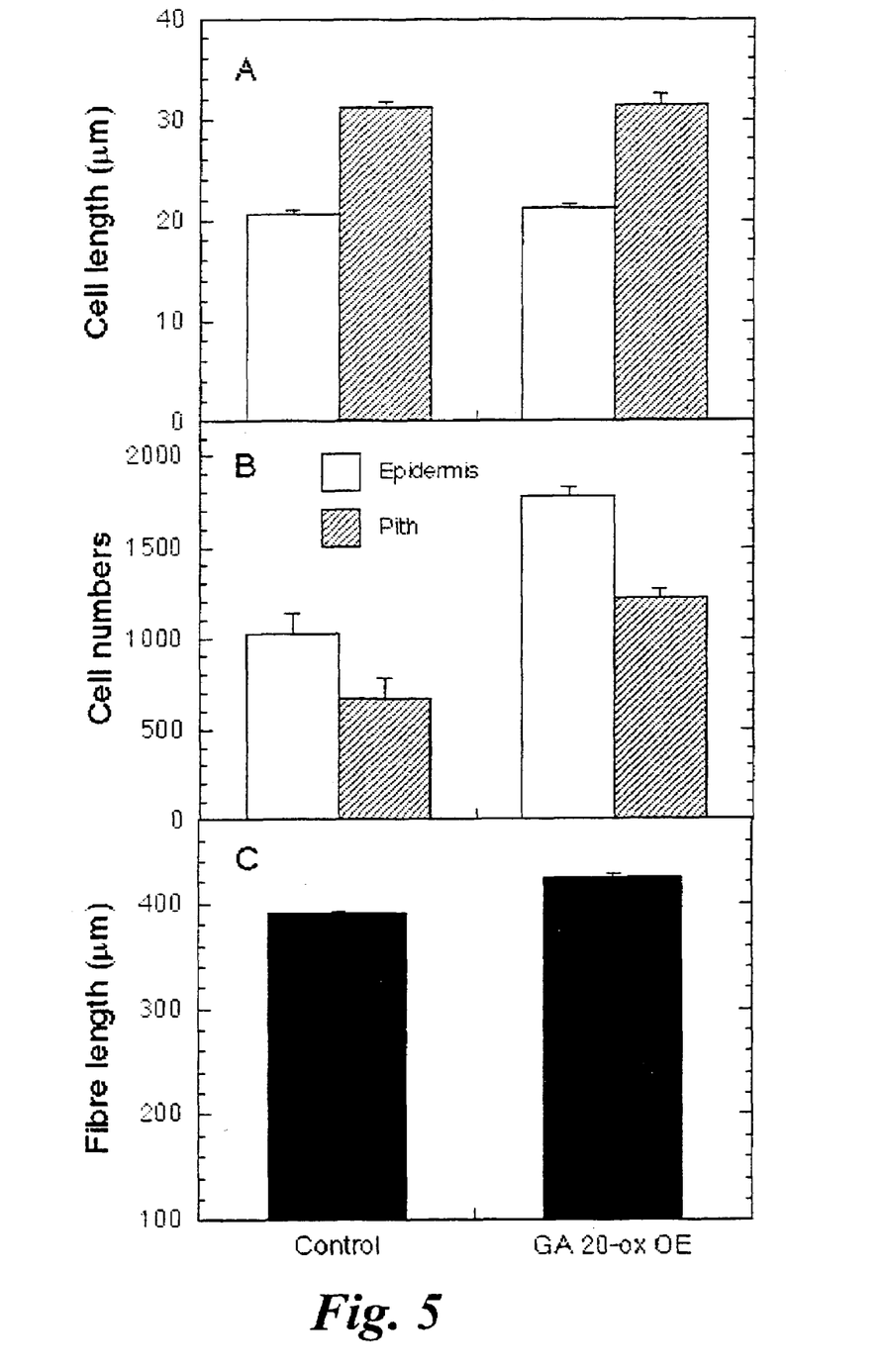
FIG. 5 illustrates the effects of GA 20-oxidase over-expression on (A) Cell lengths, (B) cell numbers per internode, (C) number of xylem fibres and (D) xylem fibre length. Cell lengths and cell numbers were measured in fully elongated internodes of actively growing plants as was number of xylem fibres. Data for the GA 20-oxidase over-expressing lines are means for nine independently generated lines, respectively. Fibre length values for non-elongating plants represent means for three independently generated lines. The vertical bars represent SE.

The observed increase in height growth (FIG. 3) in the transgenic GA 20-oxidase *Populus* trees was apparently not a consequence of increased cell elongation, as no significant changes in cell lengths were found (FIG. 5A). However, observed differences in numbers of cells per fully elongated internode clearly indicate that elevated GA levels affect cell divisions in stem tissue (FIG. 5). This is an interesting aspect of the present invention, which opens up many possibilities of influencing the production of fibrous raw material and biomass for different purposes.

Although GAs have been found to affect cell elongation, it is also known GAs can induce mitotic activity in the subapical region of the stem. It must be emphasised, however, that although samples were taken for cell length measurements from the same position for both control and transgenic plants (as defined by the number of internodes from the apex), it can not be ruled out that the cells in the transgenic plants could have been at an earlier developmental stage than in wild type plants, and they could still have been elongating. It has also been suggested that the action of GAs in meristematic tissues extends the elongation zone of the organ being formed.

TABLE 1

Concentration (ng g$^1$ fresh weight) of GAs in stem/leaf tissue from internodes 7 and 8 (see text for details) of transgenic hybrid aspen expressing the AGA20ox1 gene. Means of three independent measurements.
n.d. = not detectable.

| Genotype | $GA_{12}$ | $GA_{53}$ | $GA_{19}$ | $GA_9$ | $GA_{20}$ | $GA_4$ | $GA_1$ | $GA_{11}$ | $GA_8$ |
|---|---|---|---|---|---|---|---|---|---|
| Control | 5.78/1.15 | 3.22/0.41 | 3.15/1.21 | n.d./n.d. | 0.45/0.43 | 0.84/0.88 | 0.63/0.63 | 1.63/1.23 | 15.0/9.4 |
| Line 1 | 1.16/0.79 | 0.29/0.28 | 0.85/0.55 | 3.20/0.64 | 5.36/1.44 | 9.71/4.03 | 20.2/1.29 | 5.00/3.78 | 58.6/40.7 |
| Line 2 | 3.02/0.90 | 1.04/1.25 | 3.55/0.59 | 4.34/1.24 | 3.69/2.84 | 9.04/6.60 | 10.2/2.47 | 8.37/5.94 | 77.4/43.8 |
| Line 4 | 1.06/0.71 | 0.27/0.24 | 0.81/0.63 | 5.23/0.86 | 5.03/2.84 | 11.3/4.76 | 11.7/1.58 | 7.84/4.78 | 53.2/52.9 |
| Line 7 | 1.00/0.73 | 0.29/0.28 | 1.21/0.60 | 5.38/0.78 | 4.74/2.36 | 20.7/6.29 | 14.0/1.35 | 6.03/4.69 | 68.4/32.7 |
| Line 9 | 2.49/0.73 | 0.62/0.26 | 1.19/0.56 | 5.67/0.73 | 6.00/2.16 | 9.70/5.13 | 5.42/2.35 | 10.46/4.85 | 70.0/49.6 |
| Line 11 | 1.67/0.62 | 0.57/0.28 | 2.04/0.60 | 4.31/1.42 | 5.77/3.31 | 10.7/5.30 | 14.2/1.81 | 9.43/4.28 | 72.6/42.6 |
| Line 13 | 0.91/0.78 | 0.26/0.25 | 0.90/0.64 | 6.58/0.64 | 16.4/3.45 | 19.8/6.46 | 29.3/3.22 | 7.98/3.85 | 75.9/55.1 |
| Line 14 | 1.26/0.64 | 0.27/0.25 | 0.62/0.55 | 3.2/0.41 | 4.01/1.48 | 6.99/2.36 | 11.6/1.38 | 5.52/4.69 | 78.6/37.5 |
| Line 15 | 1.82/0.60 | — | 5.57/0.74 | — | 2.53/2.57 | 3.14/2.58 | 2.58/1.62 | 7.53/5.02 | 57.6/48.2 |

Figure 4:
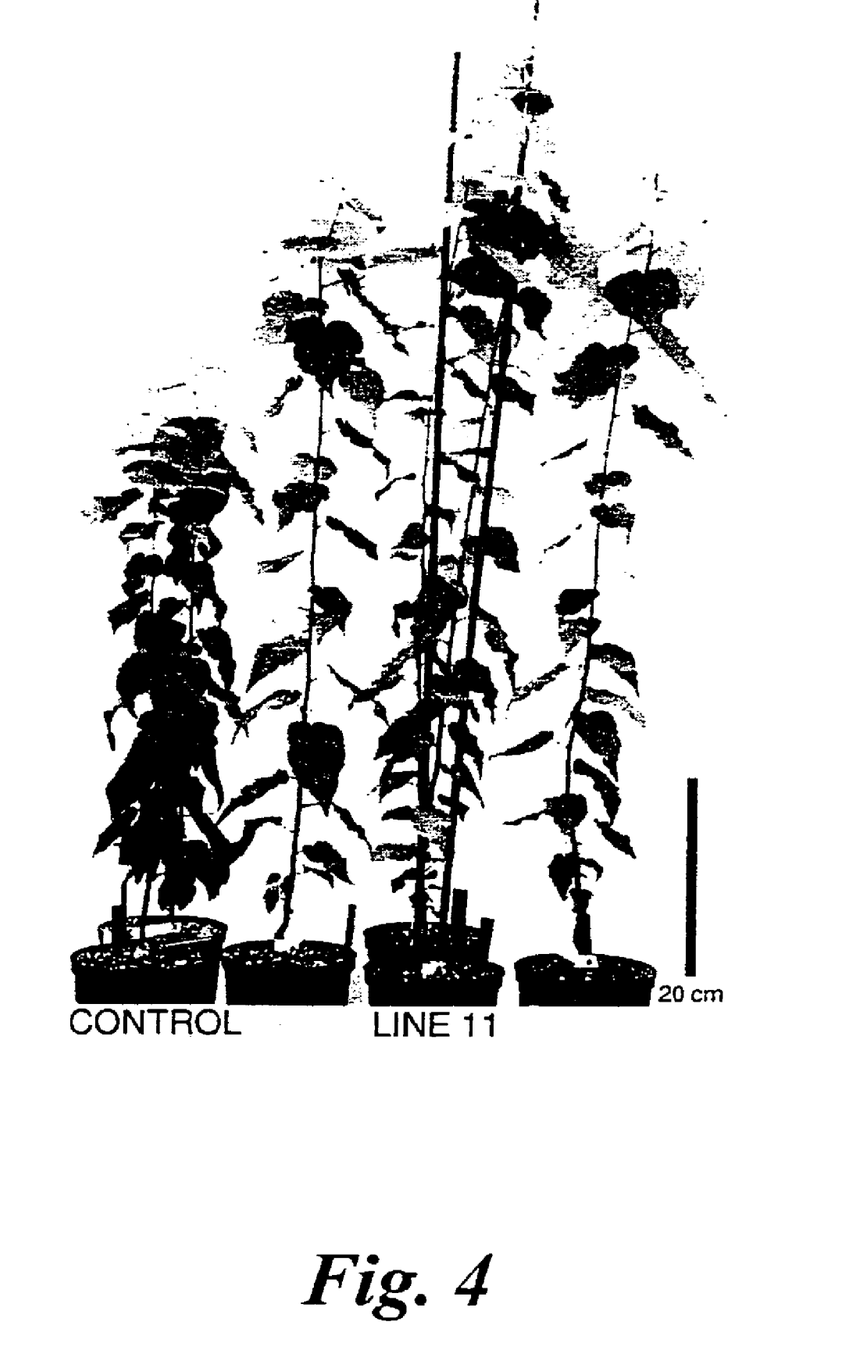
FIG. 4 is a photograph showing control and transgenic (line 11) plants after 12 weeks in the growth chamber.

Studies involving the application of plant hormones have shown that GAs can increase cambial activity in trees, especially in conjunction with IAA. Here, the engineered increase in GA levels resulted in faster stem diameter growth (FIG. 4). An effect of elevated GA levels on secondary growth was also observed with the increase in number of xylem fibre cells and xylem fibre length (FIGS. 5C, D). The length increase measured in the experiments is about 8% which must be held to be a significant increase, having consequences for the fibre properties and thus the potential uses for the fibrous raw material.

This is consistent with application studies with both GAs and inhibitors of GA biosynthesis. In *Populus*, fibre and vessel lengths increase in the transition zone between juvenile and mature wood. Therefore, the time it takes for a cell to mature within the cambial region, i.e. the time spent in the different differentiation zones, will ultimately determine its size and cell wall thickness. If the action of GAs like $GA_1$ and/or $GA_4$ extends this transition time, this would explain both the increased fibre length in the mature parts of the transgenic plant and the lack of differences in xylem fibre length between transgenic and control plants in young stem tissue.

The increase in leaf size in the transgenic plants was a result of an increase in both radial and longitudinal elongation (Table 2). At earlier stages the longitudinal growth was more pronounced, resulting in long, narrow leaves. However, at later stages the leaf morphology became similar to control plants with a similar leaf width to length ratio. It has been shown that GAs promote leaf elongation e.g. in garden pea. The very long and narrow leaves observed in constitutive GA signal mutants, like sln mutants of barley and spy mutants of *Arabidopsis*, also indicate that GAs promote leaf elongation. However, little is still known on the more specific regulatory roles of GAs in leaf development. In *Arabidopsis*, leaf blade expansion is regulated by at least two independent and polarised processes: length and width development, with ROTUNDIFOLIA and ANGUSTIFO- LIA genes playing specific roles. It is not known whether GAs modulate the cellular responses to these genes. However, it is noteworthy that leaf phenotypes in the transgenic GA 20-oxidase aspen change during development, suggesting that the two developmentally separate processes of leaf length and width growth are both affected by GAs, but at different stages.

Table 2. Morphological characterisation of wild type and transgenic hybrid aspen expressing the AtGA2ox1 gene. The numbers of plants used for the measurements were 10, 5 and 6 for the control, line 2, and line 11, respectively. In the biomass determination the numbers of plants sampled 7, 2, 3 and 23 for the control, line 2, line 11, and all sampled transgenics, pooled, respectively.

For all statistical analyses ANOVA was used to compare the plants with respect to genotype. Statistically significant difference are indicated at the 1% (*) and 5% (**) probability levels (Fisher's PLSD).

|  | Genotype | | |
| --- | --- | --- | --- |
|  | Control | Line 2 | Line 11 |
| Internode length (cm = SE) | 2.19 = 0.05 | 3.06 = 0.09* | 3.07 = 0.09* |
| Leaf length and width (cm ± SE) | | | |
| Leaf length 10 | 8.34 ± 0.36 | 9.52 ± 0.38** | 9.17 ± 0.28 |
| Leaf width 10 | 7.25 ± 0.41 | 6.28 ± 0.20 | 5.85 ± 0.24** |
| Leaf length 14 | 9.52 ± 0.45 | 11.18 ± 0.60** | 10.78 ± 0.41 |
| Leaf width 14 | 8.00 ± 0.38 | 8.35 ± 0.39 | 8.52 ± 0.25 |
| Leaf length 18 | 9.90 ± 0.79 | 11.06 ± 1.00 | 11.68 ± 0.56 |
| Leaf width 18 | 7.48 ± 0.64 | 8.80 ± 0.47 | 8.88 ± 0.43 |
| Leaf length 20 | 7.75 ± 0.34 | 11.94 ± 0.44* | 11.25 ± 0.48* |
| Leaf width 20 | 6.07 ± 0.46 | 9.44 ± 0.41* | 8.85 ± 0.41* |
| Dry Weight Biomass (g) | Control | Line 2. 11 | Transgenes |
| Leaf | 5.45 ± 0.51 | 6.38 ± 0.58 | 6.14 ± 0.28 |
| Stem | 4.58 ± 0.43 | 10.42 ± 1.01* | 10.34 ± 0.49* |
| Root | 43.05 ± 4.71 | 38.36 ± 2.63 | 37.81 ± 2.06 |
| Fresh Weight Biomass (g) | | | |
| Leaf | 17.10 ± 1.63 | 23.10 ± 2.01** | 22.05 ± 0.91** |
| Stem | 12.04 ± 1.19 | 31.39 ± 2.88* | 30.58 ± 1.28* |

Biomass measurements in transgenic and wild type plants revealed that an increase in GA 20-oxidase activity leads to a general increase in growth. This effect was especially pronounced in the stem, indicating that GAs have a strong effect on stem growth. Spraying experiments with various GAs have previously shown that these hormones tend to increase shoot biomass in *Populus* at the expense of root growth. Reductions in root formation due to increased GA levels in roots have earlier been shown in trees. In this study, poor root initiation was the major problem for survival of the transgenic GA 20-oxidase plants in tissue culture and when planting in soil. At later developmental stages, root development was still affected, but to a lesser degree (Table 2). It has also been shown that the effect of GAs on rooting varies with the stage of root development.

In conclusion, the present inventors have here demonstrated the important role of GA 20-oxidase activity in GA-controlled growth in *Populus*. It is surprising that the effects, hitherto only achieved, and in some cases only partially achieved, by external application, e.g. spraying, can be achieved by endogenous expression. It is also surprising that the inventive method can be applied to a higher species, here represented by hybrid aspen, *Populus tremula×P. tremuloides*. One important advantage of the present invention is thus that it may make it possible to reduce or eliminate the use of growth influencing chemicals in forestry.

The present invention opens up ways to genetically engineer trees to grow faster and produce more biomass simply by increasing endogenous GA levels. Interestingly, fibre lengths also increase as a result of the over-expression of the GAs. These results have both practical implications (assisting in the production of modified trees of interest to the pulp, paper and forest industries), and scientific importance, by allowing previously impossible studies on the mechanisms whereby GAs control growth and development in trees.

EXAMPLES

Experimental Protocol

Plant Vector Construction

The *Arabidopsis* GA20-oxidase cDNA construct cloned in bluescript pAt2301 [Phillips, A. L. et al. Isolation and expression of three gibberellin 20-oxidase cDNA clones from *Arabidopsis*, *Plant Physiol.* 108, 1049–1057 (1995)], recently renamed AtGA20ox1 [Coles, J. P. et al. Modification of gibberellin production and plant development in *Arabidopsis* by sense and antisense expression of gibberellin 20-oxidase genes, *Plant J.* 17, 547–556 (1999)] was obtained as a gift from P. Hedden.

An upstream ATG sequence, preceding the translational start of the GA 20-oxidase enzyme, was removed by in vitro mutagenesis. A forward primer matching the 5'-end of the GA 20 oxidase gene, but lacking the extra ATG and carrying a Bam HI and Xba I site, and a reverse primer spanning an internal Hind III site in the GA 20 oxidase gene, were used in a PCR reaction. Using AtGA20ox1 as a template, a PCR product was obtained and subcloned into the pOK12 vector, generating plasmid pOK12.GA20ox5'. An entire GA 20-oxidase cDNA lacking the extra ATG was then re-constituted, by digesting AtGA20ox1. isolating a fragment containing the 3'-end of the GA 20-oxidase gene, and ligation of this fragment into pOK12.GA20ox 5', giving plasmid pOK12/AtGA20ox1. The GA 20-oxidase cDNA was then isolated from pOK12 AtGA20ox1, by digestion with Bam HI, and ligated in sense orientation into the Bam HI site of the binary vector pPCV702.kana [Walden, R., Koncz, C. & Schell, J. Methods Mol. Cell. Biol. 1, 175–194 (1990). The use of gene vectors in plant molecular biology, *Methods Mol. Cell Biol.* 1, 175–194 (1990)], subjecting it to the control of the CaMV 35S promoter.

Plant Transformation and Growth Conditions

Hybrid aspen *Populus tremula* L.x*P. tremuloides* Michx. clone T89 was transformed and regenerated essentially as previously described [Nilsson. O. et al. Spatial pattern of cauliflower mosaic virus 35S promoter-luceferase expression in transgenic hybrid aspen trees monitored by, enzymatic assay and non-destructive imaging, *Transgenic Reaserch* 1, 209–220 (1992)]. Out of 14 independent lines, 10 were selected and multiplied by in vitro shoot culture on half-strength MS-medium containing minerals and vitamins [Murashige, T. & Skoog, F. A revised medium for rapid growth and bio-assay with tobacco tissue cultures, *Physiologia Planatarum* 15, 473–479 (1962)].

Following root initiation, the plants were dipped in Weibufix rooting powder (Svalöf Weibull AB, Hammenhög, Sweden), and potted in a fertilised peat: perlite mixture (5:1) and kept in a growth chamber at 18° C. under a photoperiod of 18 h and a relative humidity of 90%. The photon flux density of the main light period (10 h) was 175 $\mu$mol m$^{-2}$ s$^{-1}$ at 400–750 nm (Osram Power Staw HQI-TS 400 W/D lamps, Osram, Germany) and daylength extensions were given using low-intensity light (20 $\mu$mol$^{-2}$s$^{-1}$). Plants were watered daily, and repotted and fertilised with a complete nutrient solution (SuperbaS. Supra Hydro AB, Landskrona, Sweden) when needed. After 108 days some plants were transferred to short photoperiod conditions (10 h) to induce growth cessation. These plants were then cold acclimated and kept dormant at 8° C. for 4 weeks, at which point samples were taken for fibre length measurements.

Growth Measurements and Sampling

At seven weeks of age, the plants were marked at an actively growing internode at about the same position in all plants. This was used as a reference point for diameter growth measurements and for counting the internodes. The diameter, height and number of internodes of the plants were measured every $3^{rd}$ to $4^{th}$ day. The number of internodes was counted from the top to the reference point: the first internode being defined as the one below the uppermost leaf at least 1 cm long. Plants grown under long days were harvested after 100 days, using seven control plants and 25 plants representing nine transgenic individual lines (line 6 was excluded). Internodes 7 and 8, with the upper leaves included, were sampled for GA analysis and leaves from nodes 9 and 10 for northern analysis. All tissues were frozen in liquid $N_2$ immediately after sampling. For anatomical studies, the length of internodes 15 and 16 were measured, then excised and fixed immediately in FAA. All parts remaining after sampling were separated into leaf, stem and root fractions and used for fresh weight biomass determinations. Dry weight was determined after drying the samples at 55° C. for 5 days. Dormant plants consisting of three controls and five transgenes (representing lines 2, 11 and 14) were sampled at internodes 1, 10 and 20, counted from the reference point. These samples were used for maceration and subsequent fibre length measurements.

Anatomical Characterisation

Following conventional chemical fixation samples were embedded in L R White [Regan, S., Bourquin, V., Tuominen, H. & Sundberg, B. Accurate and high resolution in situ hybridization analysis of gene expression in secondary stem tissues, *Plant J.* 19, 363–369 (1999)]. Longitudinal sections for cell counts (internode 15 and 16) and transverse sections for fibre count (internode 30), 2 $\mu$m thick, were obtained and stained with toluidine blue. Numbers of epidermal and pith cells in 1 mm of the longitudinal sections were determined for 3 sections per internode. Cell length and number of cells per internode were calculated as the averages found in internodes 15 and 16. The number of xylem fibres was counted in three separate radial files (from pith to cambium) per individual and the average for each genotype (line 4, 11, 13 and control) was calculated.

Fibre Length Measurements

For fibre length determination, trimmed pieces of outer xylem from the selected internodes were prepared. The samples were macerated by boiling in a solution of 10% hydrogen peroxide and 50% glacial acetic acid for 4–6 h. When totally bleached, they were rinsed with distilled water three times, neutralised with sodium carbonate and washed again in water. Finally, the fibres were separated from each other by shaking in water and measured using a fibre analyser (KAJAANI FiberLab, Valmet Automation Kajaani Ltd, Kajaani, Finland). On average, the lengths of 30 800 fibres per sample were measured.

Northern Analysis

Total RNA was extracted from leaves using a chloroform and hexadecyltrimethylamonium bromide based method according to Chang et al. [Chang, S., Purvear, J. & Cairney, J. A simple and efficient method for isolating RNA from pine trees, *Plant Mol. Biol. Rep.* 1, 13–116 (1993)]. About 18 $\mu$g of total RNA per sample was separated in a formaldehyde agarose gel according to Sambrook et al. [Sambrook, J., Fritsch, E. & Maniatis, T. *Molecular Cloning: A Laboratory Manual*, Cold Spring Harbor Laboratory Press. New York, 1989], and blotted on to a nylon Hybond-N membrane (Amersham, Little Chalfont, UK) according to the manufacturer's protocol. A Bam HI/Xho 1 fragment recovered from pOK12/AtGA20ox1 and an ubiquitin-like Expressed Sequence Tag (EST A046p57) obtained in the *Populus* sequencing project [Sterky, F. et al. Gene discovery in the wood-forming tissues of poplar: Analysis of 5,692 expressed sequence tags, *Proc. Natl. Acad. Sci. USA* 95, 13330–13335 (1998)] were used as probes for analysis of ectopic AtGA20ox1 and reference gene expression, respectively. Hybridisation was performed in Church buffer [Church, G. M. & Gilbert, W., Genomic sequencing, *Proc. Natl. Acad. Sci. USA* 81, 1991–1995 (1984)] at −65° C. overnight. The membrane was washed at 65° C., two times three minutes in each of solution: 2×SSPE, 0.1% SDS: 1×SSPE, 0.1% SDS: 0.5×SSPE, 0.1% SDS and 0.1×SSPE, 0.1% SDS. To visualise the expression patterns, the membrane was exposed to a phosphor imager (Molecular Imager GS-525, Bio-Rad Laboratories, Hercules, Calif. U.S.A.) overnight.

Quantification of Gibberellins

Samples of 200–300 mg were ground in liquid nitrogen to a homogenous powder, and GAs were analysed as earlier described by Peng et al. [Peng, J. R., Richards, D. E., Moritz, T., CanoDelgado, A. & Harberd, N. P., Extragenic suppressors of the *Arabidopsis* gai mutation alter the dose-response relationship of diverse gibberellin responses, *Plant Physiol.* 119, 1199–1207 (1999)] with a few modifications. Volumes of the solvents used for extraction and partitioning, and that of the anion-exchange column, were reduced. Furthermore, the samples were methylated prior to the HPLC step, and finally they were analysed by GC/MS-selected reaction monitoring (SRM) using a JEOL SX/SX102A four sector mass spectrometer (JEOL, Tokyo, Japan). [$^2H_2$]-GAs were used as internal standards.

RESULTS

Generation of Transgenic GA 20-oxidase Hybrid Aspen

Figure 6:
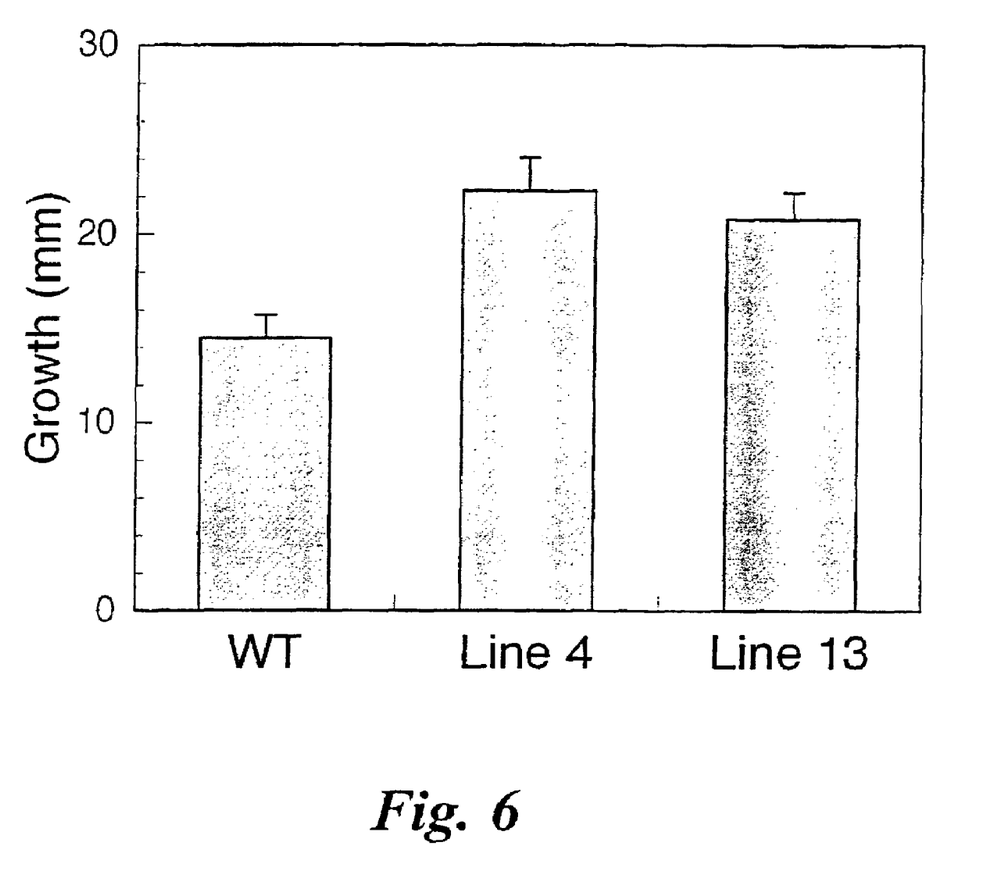
FIG. 6 shows that there is enhanced diameter growth of transgenic hybrid aspen also in the second growth season. The cumulative diameter growth of control (WT) and line 4 and 13 was determined under a period of 2.5 month, beginning after breaking of dormancy.

Out of 14 independently transformed lines, 10 were regenerated and selected for further analysis. Southern analysis showed that all the selected transgenic lines have one to three copies of the AtGA20ox1 gene inserted into their genomes, except for line 6, which has at least 4 copies (data not shown). Northern analysis of RNA isolated from leaf tissue showed that the strongest expression of the AtGA20ox1 gene was in lines 2, 7, 9, 14 and 15. Expression was slightly lower in lines 1, 4, 11 and 13, while expression was almost undetectable in line 6 (FIG. 6). In general, the transgenic lines showed poorer rooting than the control plants, both under tissue culture conditions and when potted in soil. When potted, for example, 100% of the control plants survived, compared to only 32% of the transgenic plants.

GA Levels

GA content was determined both in leaves and internodes of actively growing tissue. Transgenic plants showed high levels of the 13-hydroxylated $C_{19}$-GAs ($GA_{20}$-$GA_1$ and $GA_8$) and the non 13-hydroxylated $C_{19}$-GAs ($GA_9$, $GA_4$ and $GA_{34}$) in both stem and leaves (Table 1). The increase over wild type levels was more pronounced in stem tissue than in leaf tissue. The levels of the biologically active $GA_1$ and $GA_4$ in stem tissues of lines 7 were 22- and 24-fold higher, respectively, than in the control. Furthermore, all transgenic lines showed lower levels of the substrates for the GA 20-oxidase. For example $GA_{12}$ and $GA_{53}$ levels in stem tissues of line 7 were 17% and 9% of the contents in the control, respectively.

Shoot Growth and Morphology

Figure 2:
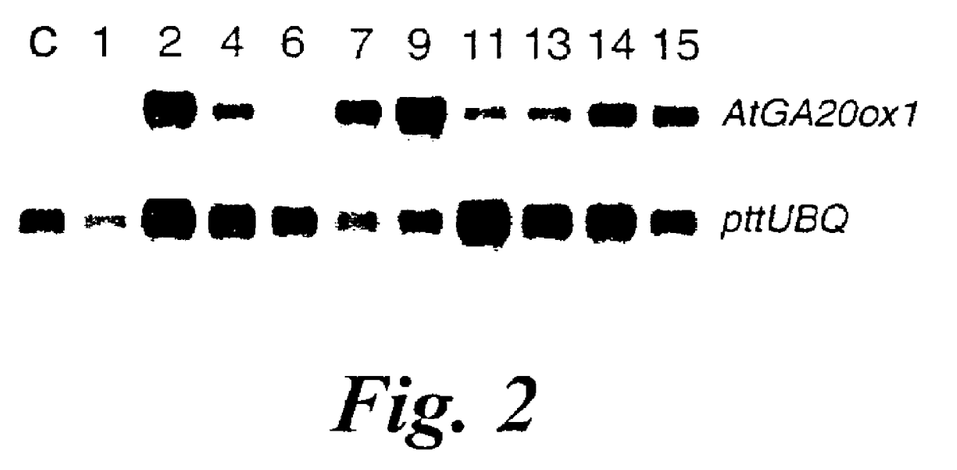
FIG. 2 shows a Northern analysis of ten GA 20-oxidase over-expressing lines (numbers 1 to 15) and the non-transformed control (C). 18 µg of total RNA was loaded from each sample, and probed with a labelled fragment isolated from *Arabidopsis* gibberellin 20-oxidase (AtGA20ox1) cDNA or from an endogenous ubiquitin (UBQ) EST sequence (pttUBQ).

All transgenic lines showed faster than wild type height and diameter growth (FIG. 3), giving the trees a characteristic phenotype (FIG. 4). Although levels of GA 20-oxidase mRNA varied between the transgenic lines (FIG. 2) there were no strict correlation between expression levels and growth. A detailed study of two of the transgenic lines (Table 2) revealed that the difference in height growth was primarily due to differences in internode lengths. No statistically significant differences in the number of nodes (leaves) were observed (data not shown). However, leaf development was different in the transgenic lines. Young expanding leaves had a different morphology and a higher leaf length to width ratio than leaves of control plants (Table 2). After node 14, i.e. in the fully expanded leaves, there was no significant difference in this morphological ratio, but there was still a clear difference in leaf size between control and transgenic plants. The transgenics had longer and broader leaves and, consequently, higher mean leaf fresh weights (Table 2). Furthermore, the petioles were longer in the transgenic lines than in the control (data not shown).

There was a significant difference in shoot biomass between transgenic and control plants when measured either on a fresh or dry weight basis (Table 2). The transgenic plants had 64% higher shoot dry weight, on average, than the control plants. This difference was especially pronounced in the stem, where the transgenic plants had 126% higher dry weight than the control plants. Consequently, the transgenic plants also had an altered root:shoot weight ratio, of only about 2:1 compared to 4:1 for control plants. Although the initial rooting capacity was lower in the transgenic lines, there was no significant difference in root dry weight between transgenic and control plants (Table 2).

Cell Length and Cell Numbers in Transgenic Plants

Expression of the AtGA20ox1 gene did not effect the lengths of epidermal and pith cells in presumably fully elongated internodes (see Experimental Protocol for definition) in the actively growing transgenic lines (FIG. 5A). However, epidermal and pith cell numbers in these elongated internodes were approximately 55% higher than in the wild type control (FIG. 5B).

Cambial activity was also determined by counting numbers of xylem fibre cells in transverse sections (FIG. 5C). The transgenic lines show 71% increase in number of xylem fibre cells compared to the control plants. Xylem fibres were sampled at three different positions in dormant plants and their lengths were measured. No differences in fibre length from different heights in the trees were detected (data not shown), but the xylem fibres were approximately 8% longer in the transgenic lines than in the control plants (FIG. 5C).

Although the invention has been described with regard to its preferred embodiments, which constitute the best mode presently known to the inventors, it should be understood that various changes and modifications as would be obvious to one having the ordinary skill in this art may be made without departing from the scope of the invention as set forth in the claims appended hereto.

The invention claimed is:

1. A transgenic plant cell of a woody plant comprising SEQ ID NO:1.

2. The transgenic plant cell of claim 1, wherein the transgenic plant cell is of the *Populus* species.

3. The transgenic plant cell of claim 1, wherein the transgenic plant cell is obtained from a *Populus tremula×P. tremuloides* cross.

* * * * *